United States Patent
Dai et al.

(10) Patent No.: US 10,782,372 B2
(45) Date of Patent: Sep. 22, 2020

(54) MAGNETIC RESONANCE IMAGING SYSTEM RADIO FREQUENCY SUBSYSTEM AND COIL DECOUPLING APPARATUS AND METHODS USED THEREIN

(71) Applicant: GE Precision Healthcare LLC, Wauwatosa, WI (US)

(72) Inventors: Qingyu Dai, Beijing (CN); Haoyang Xing, Beijing (CN); Yu Liu, Beijing (CN); Chun Lai Xiao, Beijing (CN); Sheng Tong, Beijing (CN); Weinan Tang, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 128 days.

(21) Appl. No.: 15/720,724

(22) Filed: Sep. 29, 2017

(65) Prior Publication Data
US 2018/0095149 A1    Apr. 5, 2018

(30) Foreign Application Priority Data

Sep. 30, 2016    (CN) .......................... 2016 1 0874137

(51) Int. Cl.
| | | |
|---|---|---|
| *G01R 33/422* | (2006.01) | |
| *G01R 33/36* | (2006.01) | |
| *G01R 33/3415* | (2006.01) | |
| *A61B 5/055* | (2006.01) | |
| *G01R 33/385* | (2006.01) | |
| *G01R 33/56* | (2006.01) | |
| *G01R 33/34* | (2006.01) | |

(52) U.S. Cl.
CPC ............ *G01R 33/422* (2013.01); *A61B 5/055* (2013.01); *G01R 33/3415* (2013.01); *G01R 33/365* (2013.01); *G01R 33/3657* (2013.01); *G01R 33/3854* (2013.01); *G01R 33/56* (2013.01); *G01R 33/34076* (2013.01)

(58) Field of Classification Search
None
See application file for complete search history.

(56) References Cited

U.S. PATENT DOCUMENTS

| | | | | |
|---|---|---|---|---|
| 2005/0200358 A1* | 9/2005 | Boskamp | ......... | G01R 33/34046 324/318 |
| 2015/0323628 A1* | 11/2015 | Wald | .................. | G01R 33/3415 324/309 |
| 2017/0248673 A1* | 8/2017 | Kang | .................... | A61B 5/055 |

* cited by examiner

*Primary Examiner* — Douglas X Rodriguez
(74) *Attorney, Agent, or Firm* — Armstrong Teasdale LLP

(57) ABSTRACT

A magnetic resonance imaging (MRI) system radio frequency (RF) subsystem and a coil decoupling apparatus and method used therein. The MRI system RF subsystem comprises a body coil and a surface coil for receiving MR signals, and also comprises a preamplifier for amplifying the MR signals received by the body coil; the coil decoupling apparatus comprises a phase shifter, which is connected between the preamplifier and the body coil, and used for receiving an external voltage regulation signal to regulate an operation voltage thereof, wherein the voltage regulation signal is determined according to a current patient's weight.

13 Claims, 4 Drawing Sheets

MAGNETIC RESONANCE IMAGING SYSTEM RADIO FREQUENCY SUBSYSTEM AND COIL DECOUPLING APPARATUS AND METHODS USED THEREIN

CROSS-REFERENCE TO RELATED APPLICATIONS

This application claims priority to Chinese Patent Application No. 201610874137.9, filed on Sep. 30, 2016, the entirety of which is incorporated herein by reference.

BACKGROUND

The present invention relates to a medical imaging field, particularly to a magnetic resonance imaging (MRI) systems radio frequency (RF) subsystem and a coil decoupling apparatus and method used therein.

A MRI system usually has a magnet subsystem, an RF subsystem, a gradient subsystem, a signal acquisition subsystem, an image reconstruction subsystem and a computer control subsystem.

In a magnetic resonance (MR) RF subsystem, RF excitation pulses, after being amplified by an RF power amplifier, are divided through an I/Q dual-branch switch into two branches of signals including I and Q to be transmitted to a body coil, then the body coil generates RF excitation signals to excite a human body to generate MR signals. After the RF excitation is finished, the I/Q dual-branch switch is switched from a transmitting mode to a receiving mode. In the receiving mode, the body coil may serve as a receiving coil for receiving the MR signals that may also be received by a surface coil. A preamplifier is provided on a receiving link of the MR signal, in which the preamplifier is coupled to the I/Q dual-branch switch, and the MR signals received by the body coil are transmitted to the preamplifier for amplifying via the I/Q dual-branch switch, and then are acquired by a data acquisition subsystem for image reconstruction.

In the prior art, an MRI method is put forward, wherein in the receiving mode, the body coil and the surface coil receive the MR signals simultaneously, and an image reconstruction is performed on the signals acquired from the surface coil, utilizing the signals acquired from the body coil as reference signals, which can improve signal to noise ratio (SNR) of the image.

However, when scanning a patient, it is found that a decoupling performance of the body coil will decrease due to the patient's weight, which reduces the SNR of the image, affecting the image quality.

SUMMARY

One objective of the present invention is to provide a new MR RF subsystem and a coil decoupling apparatus and method used therein, which can improve decoupling performance of a body coil and improve SNR of an image.

Exemplary embodiments of the present invention provide a coil decoupling apparatus for an MR RF subsystem, the MR RF subsystem comprising a body coil and a surface coil for receiving MR signals, and also comprising a preamplifier for amplifying the MR signals received by the body coil; the coil decoupling apparatus comprises a phase shifter which is connected between the preamplifier and the body coil and used for receiving an external voltage regulation signal to regulate an operation voltage thereof, where the voltage regulation signal is determined according to a current patient's weight.

Exemplary embodiments of the present invention further provide an MR RF subsystem, comprising a body coil and a surface coil used for receiving MR signals from the patient, and a preamplifier for amplifying the MR signals received by the body coil, further comprising a coil decoupling apparatus as described above.

Exemplary embodiments of the present invention also provide a coil decoupling method for an MR RF subsystem, wherein the MR RF subsystem comprises a body coil and a surface coil for receiving MR signals, and a preamplifier for amplifying the MR signals received by the body coil. A phase shifter is connected between the preamplifier and the body coil. The coil decoupling method comprises: acquiring a patient's weight; determining a voltage value corresponding to the current patient's weight according to a correspondence relationship between a pre-stored patient's weight and a voltage value; and sending a voltage regulation signal to the phase shifter to regulate the operation voltage of the phase shifter to the determined voltage value described above.

Other features and aspects will be apparent through the following detailed description, figures and claims.

BRIEF DESCRIPTION OF THE DRAWINGS

The present invention can be understood better in light of the description of exemplary embodiments of the present invention with reference to the accompanying drawings, in which.

DETAILED DESCRIPTION

Figure 1:
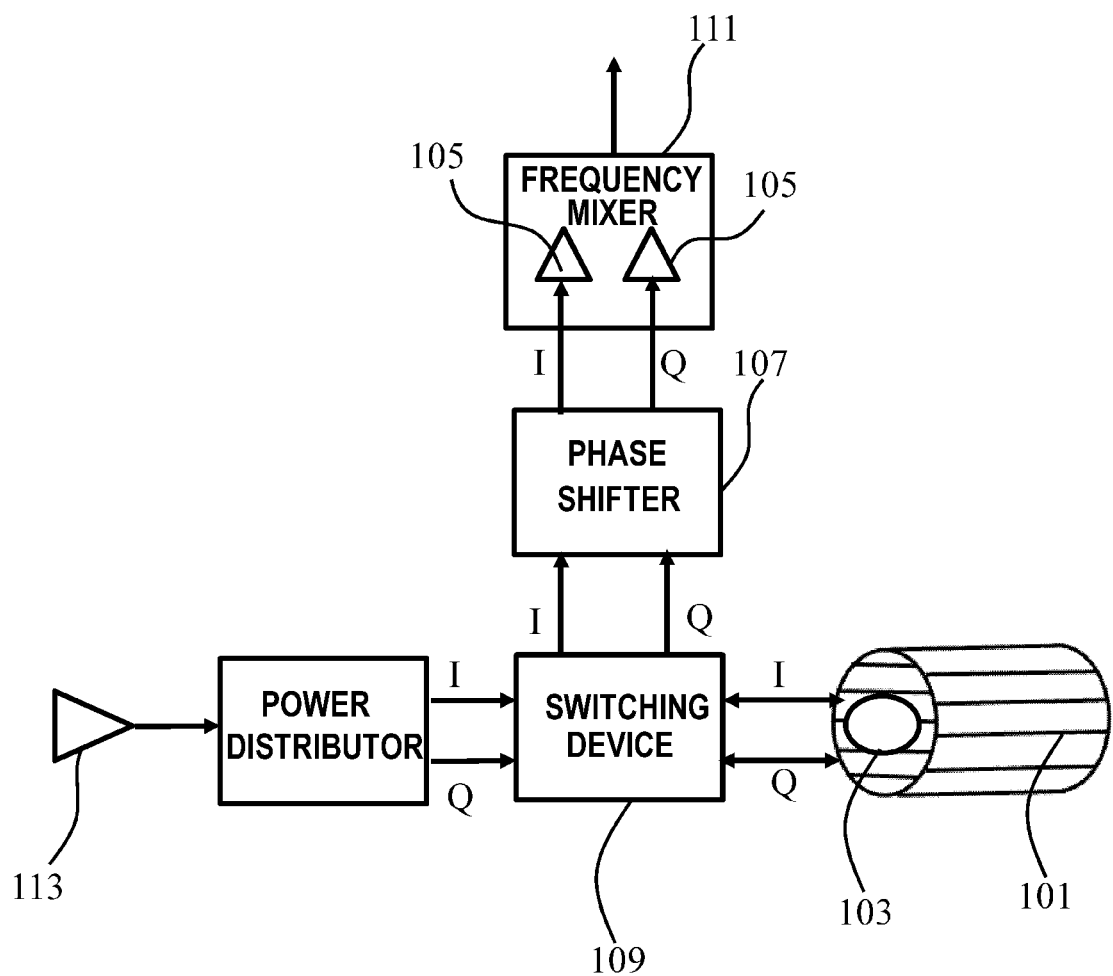
FIG. 1 is a schematic structural diagram of an MR imaging subsystem provided in one embodiment of the present invention, the MR imaging subsystem comprising a coil decoupling apparatus.

Hereafter, a detailed description will be given for preferred embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for one of ordinary skilled in the art associated with the contents disclosed in the present disclosure, which should not be regarded as insufficient disclosure of the present disclosure.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present application for invention do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

The MR imaging method in embodiments of the present invention can be used in an MR imaging equipment to obtain an MR image of a part-to-be examined of the patient. It will be appreciated by one skilled in the art that the MR imaging equipment may comprise a main magnet for generating a main magnetic field, an RF system for generating an RF field, and a gradient system for generating a gradient field. The RF system may comprise a body coil and a receiving coil, where the body coil may function as an RF transmitting coil and an RF receiving coil, and a surface coil may function as an RF receiving coil. The MR imaging equipment may also comprise a computer system, which may control a pulse generator to generate RF pulses, gradient pulses, etc.

FIG. 1 is a schematic structural diagram of an MR RF subsystem provided in one embodiment of the present invention, wherein the RF subsystem comprises a coil decoupling apparatus used therein. As shown in FIG. 1, the MR RF subsystem comprises a body coil 101, a surface coil 103 and a preamplifier 105, wherein the surface coil 103 may be placed in a hole of the body coil 101 for imaging. The body coil 101 and the surface coil 103 may be used to receive MR signals generated by a human body. The preamplifier 105 may amplify the MR signals received by the body coil 101. The amplified MR signals may be acquired by a data acquisition subsystem. Image reconstruction may be performed by an image reconstruction subsystem of the MR RF subsystem based on the acquired data. The MR signals received by the surface coil 103 may be acquired by the data acquisition subsystem via another path.

In an embodiment, of the present invention, the body coil 101 and the surface coil 103 may receive MR signals simultaneously, and the signal coupling generated by the body coil 101 to the surface coil is removed by introducing a high resonance impedance between the body coil 101 and the preamplifier 105. In other embodiments, the body coil 101 may also only function as an RF transmitting coil, or one of the body coil 101 and the surface coil 103 is used for receiving MR signals.

The coil decoupling apparatus according to an embodiment of the present invention comprises a phase shifter 107 connected onto a signal receiving path between the preamplifier 105 and the body coil 101, the surface coil 103, and used for receiving an external voltage regulation signal to regulate an operation voltage thereof, where the voltage regulation signal is determined according to a current patient's weight.

The above signal receiving path between the preamplifier 105 and the body coil 101, i.e., a signal transmission line through which the MR signals received by the body coil 101 are transmitted to the preamplifier 105, for example, comprises a transmission line between the body coil 101 and the preamplifier 105.

Figure 2:
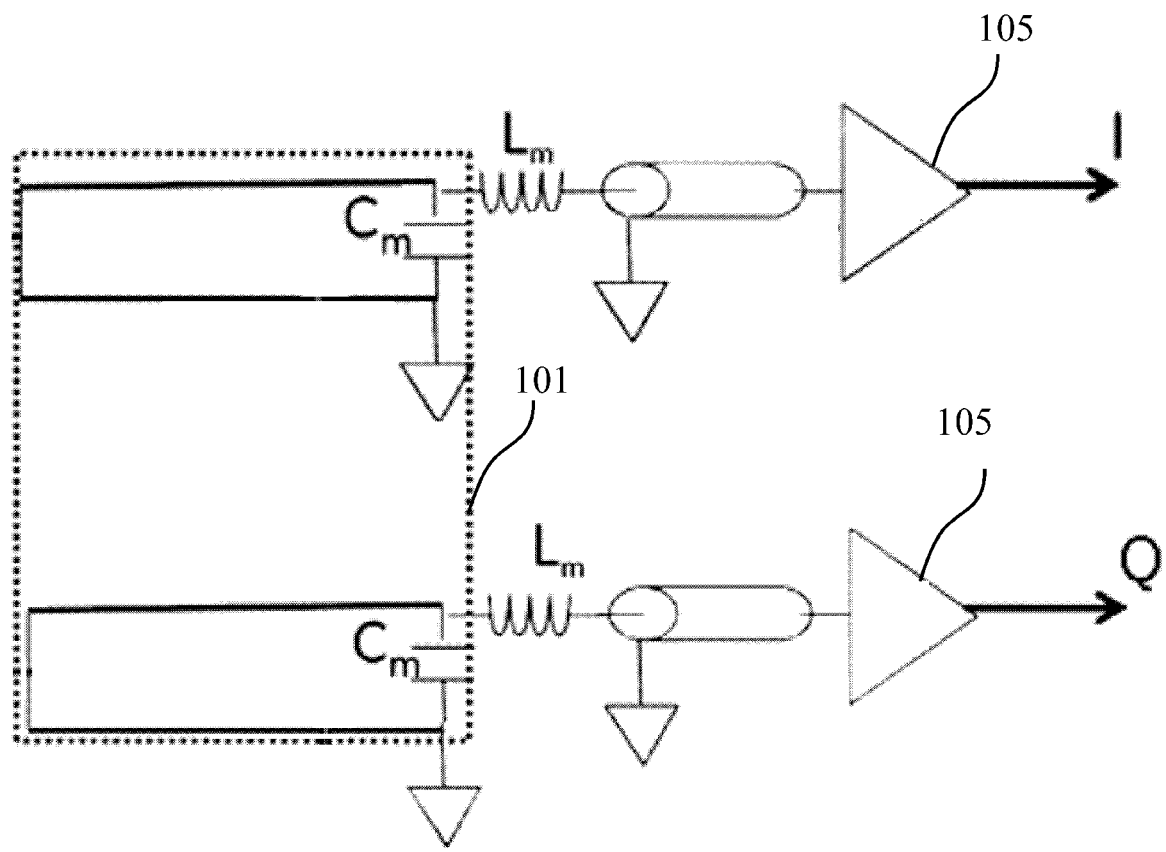
FIG. 2 is a principle diagram of removing a coupling between a body coil and a surface coil by utilizing an LC resonant impedance.

FIG. 2 is a principle diagram of removing the coupling between the body coil and the surface coil by utilizing an LC resonant impedance. As shown in FIG. 2, an induction capacitance C_m on the body coil 101 is utilized to achieve impedance matching with the transmission line (which can be regarded as an induction inductance L_m), to produce a high resonance impedance between the body coil 101 and the preamplifier 105, so as to remove the signal coupling of the body coil 101 to the surface coil disposed therein. As shown by combining FIG. 1, when an effect of the patient's weight leads to a change in the induction capacitance C_m, it may cause the decoupling performance of the body coil 101 to the surface coil 103 to be reduced, and at this moment the phase of the transmission line may be changed by the phase shifter 107, thereby regulating the impedance thereof, so as to reduce the signal coupling between the body coil 101 and the surface coil 103, enhancing the decoupling performance.

Figure 3:
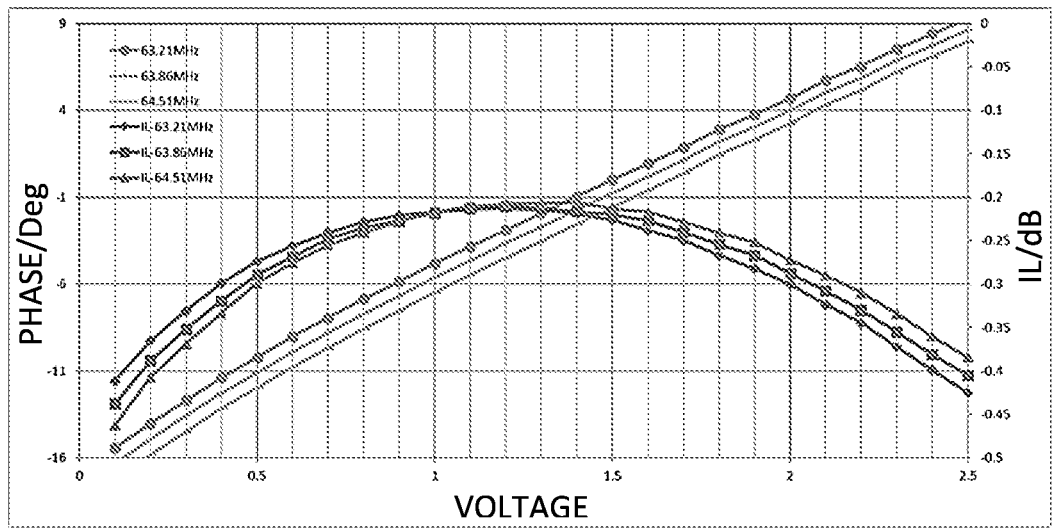
FIG. 3 shows correspondence relationships between operation voltages and their phases of the phase shifter in FIG. 1 at different signal frequencies.
Figure 4:
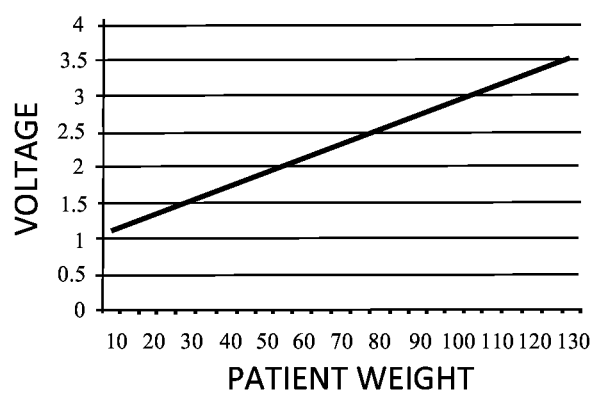
FIG. 4 shows a correspondence relationship between a patient's weight and an operation voltage of the phase shifter.

FIG. 3 shows correspondence relationships between operation voltages and their phases of the phase shifter at different signal frequencies. FIG. 4 shows a correspondence relationship between patient's weights and operation voltages of the phase shifter.

When the phase shifter 107 is connected on the transmission line, the phase delay of the electromagnetic wave on the signal transmission line may be regulated by regulating the operating voltage of the phase shifter, thereby the output impedance of the signal transmission line and the resonance impedance between the signal transmission line and the capacitor on the body coil 101 are regulated. Referring to FIG. 3, it can be seen that, for the signal coupling between coils caused by the patient's weight, a phase delay may be achieved by regulating the operation voltage through testing the current output impedance of the transmission line when performing scan on volunteers with different weights, and estimating the phase delay required to achieve an optimized impedance value.

In one embodiment, the current output impedance may be tested by simulation. For example, a simulation device is connected at a contact point of the transmission line and the body coil, to acquire an output impedance of the transmission line.

The operation voltages of the phase shifter required for different patients' weights may be known from a correspondence relationship shown in FIG. 4, so as to reduce or remove the electromagnetic coupling between the body coil 101 and the surface coil 103 introduced by the effect of the patient's weight. Therefore, in the embodiment of the present invention, it is possible to compensate for the decrease of the decoupling performance caused by the patient's weight by applying a determined operating voltage to the phase shifter.

As shown in FIG. 1, a switching device 109 may also be provided on the signal receiving path between the preamplifier 105 and the body coil 101, the surface coil 103. The switching device 109 described above may comprise an I-branch of switch and a Q-branch of switch, and the preamplifier 105 may comprise a first preamplifier and a second preamplifier, wherein the first preamplifier is coupled to the I-branch of switch and the second preamplifier is coupled to the Q-branch of switch.

The switching device 109 may be switched between an RF receiving mode and an RF transmitting mode. When it is in the RF transmitting mode, the RF excitation pulse signal is divided into two branches, i.e., I-branch and Q-branch, via a power distributor, and both of the I-branch and Q-branch of switches are in a first position, to turn on the signal path between the body coil 101 and an RF power amplifier 113, then the two branches of RF excitation pulse signals are transmitted to the body coil 101 via the I-branch and the Q-branch respectively and emitted to a human body to excite protons inside the human body to produce resonance. When it is in the RF receiving mode, both of the I-branch and Q-branch of switches are in a second position, to turn on the signal path between the body coil 101 and the preamplifier 105, then the MR signals received by the body coil 101 from the human body are transmitted to the preamplifier via the I-branch of switch and the Q-branch of switch for amplifying.

In one embodiment of the present invention, the phase shifter 107 may be connected between the preamplifier 105 and the switching device 109, for example, on a transmission line between the switching device 109 and the preamplifier 105, or integrated in the switching device 109.

The RF subsystem according an embodiment of the present invention may further comprise a frequency mixer 111 for mixing frequencies of the MR signals output from the first preamplifier and the second preamplifier. The preamplifier 105 may be integrated in the frequency mixer 111, and the phase shifter 107 may also be integrated in the frequency mixer 111.

In other embodiments, when the phase shifter is not suitable to be connected between the preamplifier 105 and the switching device 109 for some reasons, the phase shifter 107 may also be connected between the switching device 109 and the body coil 101 with greater cost.

The voltage regulation signal described above may be generated by a control device external to the MR RF subsystem and transmitted to a voltage adapter of the MR RF subsystem, to control the voltage adapter to provide a required operation voltage for the phase shifter 107.

A voltage regulation module may also be provided in the MR RF subsystem, wherein the voltage regulation module may acquire a current patient's weight, determine a voltage value corresponding to the current patient's weight according to a correspondence relationship between a pre-stored patient's weight and a voltage value, and send a voltage regulation signal to the phase shifter 107 to regulate the operation voltage of the phase shifter 107 to the determined voltage value.

Figure 5:
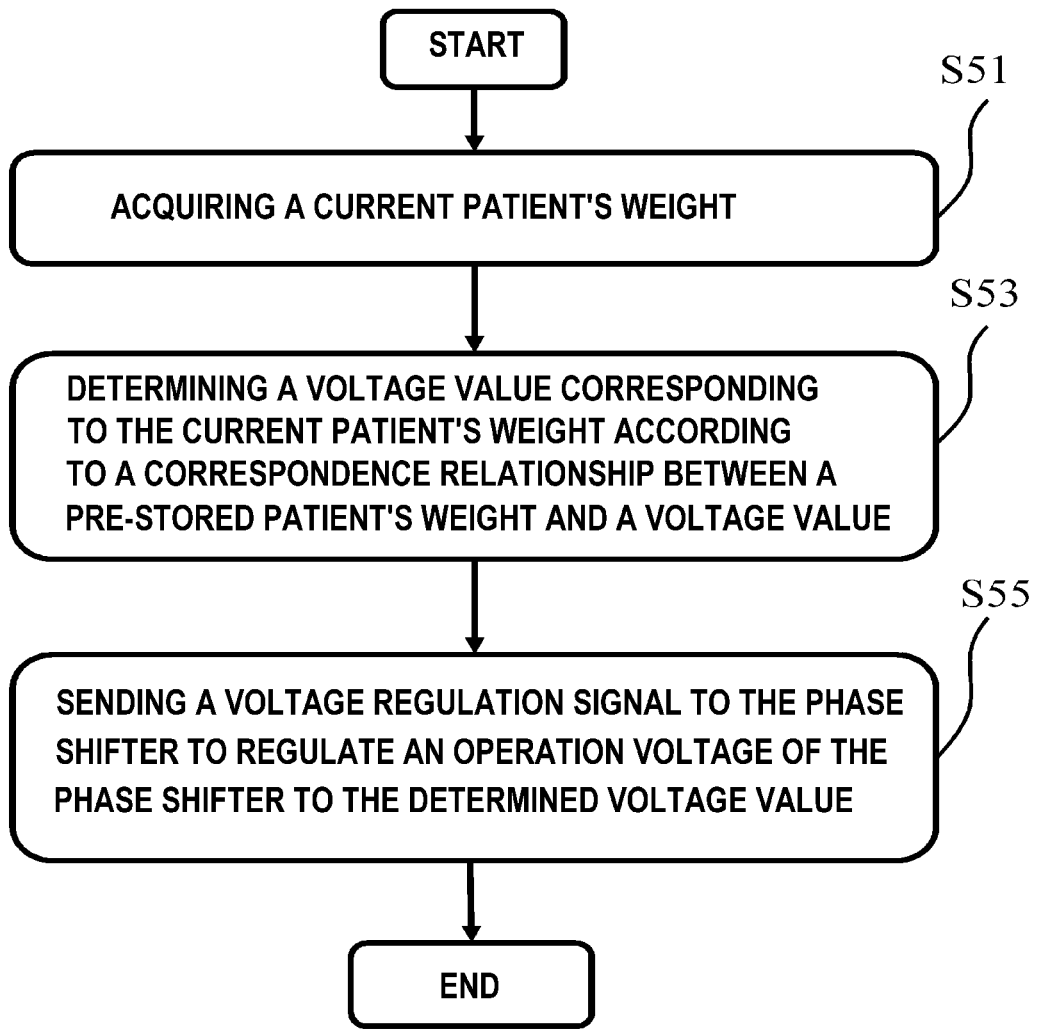
FIG. 5 is a coil decoupling method for an MR imaging subsystem provided in one embodiment of the present invention.

FIG. 5 is a flow chart of a coil decoupling method provided by one embodiment of the present invention. The method may be used in the MR RF subsystem of the embodiments described above. As shown in FIG. 5, the coil decoupling method comprises the following steps: Step S51: acquiring a current patient's weight; Step S53: determining a voltage value corresponding to the current patient's weight according to a correspondence relationship between a pre-stored patient's weight and a voltage value; and Step S55: sending a voltage regulation signal to the phase shifter 107 to regulate an operation voltage of the phase shifter to the determined voltage value.

Specifically, in the above correspondence relationship between a pre-stored patient's weight and a voltage value, the voltage value increases as the patient's weight increases.

For example, when the patient has a weight of 70 kg, the phase delay of the phase shifter 107 needs to be −16 degrees to make the transmission line reach an optimized impedance value, and a voltage of 0 volt needs to be applied to the phase shifter 107 at this moment; when the patient has a weight of 100 kg, the phase delay of the phase shifter 107 needs to be 4 degrees to make the transmission line reach the optimized impedance value, and a voltage greater than 0 volt needs to be applied to the phase shifter 107 at this moment. Those values of the phases, patient's weights and voltages described above are only for exemplary purpose, and may be different in practical cases.

Optionally, prior to determining a voltage value corresponding to the current patient's weight according to a correspondence relationship between a pre-stored patient's weight and a voltage value, a step of acquiring the correspondence relationship between a patient's weight and a voltage value is further included, which may comprise the following steps: 1) acquiring the patient's weight and measuring an output impedance of a transmission line between the body coil and the preamplifier when performing a scan on the patient; 2) regulating a phase of the transmission line by regulating the operation voltage of the phase shifter 107, until the measured output impedance is equal to an optimized value; and 3) storing a correspondence relationship between the operation voltage and the patient's weight.

Optionally, "measuring an output impedance of a transmission line between the body coil 101 and the preamplifier 105" may comprise: acquiring the output impedance of the transmission line by connecting a simulation equipment at a contact point of the transmission line and the body coil 101.

The embodiments of the present invention apply a corresponding voltage to a phase shifter according to different patients' weights, to finely regulate the phase delay of the phase shifter, thus optimizing a transmission impedance of its connected transmission line (which is connected between a body coil and a preamplifier), so as to compensate for the problem of the decrease of the decoupling performance between the body coil and the surface coil caused by the patient's weight. When the present invention is applied in an MR imaging system which utilizes both of the body coil and the surface coil to receive MR signals, the system stability can be improved by compensating for the environment influence, so that the SNR of the acquired image is kept at a higher level.

Some exemplary embodiments have been described in the above. However, it should be understood that various modifications may be made thereto. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other implementation also falls within a protection range of the claims.

What is claimed is:

1. A coil decoupling apparatus for a magnetic resonance (MR) radio frequency (RF) subsystem, the MR RF subsystem comprising a body coil and a surface coil both configured to receive MR signals generated by a patient, the body coil and surface coil configured to decouple from each other, and the MR RF subsystem also comprising a preamplifier configured to amplify the MR signals received by the body coil, the coil decoupling apparatus comprising:
a phase shifter electrically connected between the preamplifier and the body coil, wherein the phase shifter is configured to receive a voltage regulation signal determined according to the patient's weight and configured to shift phase of the MR signals received by the body coil according to the voltage regulation signal, wherein the voltage regulation signal corresponds to a phase of the phase shifter that is configured to compensate for a decrease in signal decoupling between the body coil and the surface coil caused by the patient's weight.

2. The coil decoupling apparatus of claim 1, wherein a switching device is connected between the preamplifier and the body coil, and the phase shifter is connected between the preamplifier and the switching device.

3. The coil decoupling apparatus of claim 2, wherein the switching device is configured to switch between an RF receiving mode and an RF transmitting mode, a signal receiving path between the preamplifier and the body coil is turned on to transmit the MR signals received from the patient by the body coil to the preamplifier when the switching device is switched to the RF receiving mode, wherein the surface coil receives the MR signals from the patient while the body coil receives the MR signals from the patient.

4. The coil decoupling apparatus of claim 3, wherein the switching device comprises an I-branch of switch and a Q-branch of switch, the preamplifier comprising a first preamplifier coupled to the I-branch of switch and a second preamplifier coupled to the Q-branch of switch, the MR RF subsystem further comprising a frequency mixer for mixing frequencies of the MR signals output from the first preamplifier and the second preamplifier, the phase shifter being integrated in the frequency mixer.

5. The coil decoupling apparatus of claim 2, wherein the phase shifter is integrated in the switching device.

6. The coil decoupling apparatus of claim 2, wherein the phase shifter is connected on a transmission line between the preamplifier and the switching device.

7. A magnetic resonance (MR) radio frequency (RF) subsystem, comprising:
 a body coil and a surface coil both configured to receive MR signals from a patient and configured to decouple from each other;
 a preamplifier for amplifying the MR signals received by the body coil; and
 a phase shifter electrically connected between the preamplifier and the body coil, wherein the phase shifter is configured to receive a voltage regulation signal determined according to the patient's weight and configured to shift phase of the MR signals received by the body coil according to the voltage regulation signal, wherein the voltage regulation signal corresponds to a phase of the phase shifter that is configured to compensate for a decrease in signal decoupling between the body coil and the surface coil caused by the patient's weight.

8. The MR RF subsystem of claim 7, further comprising a voltage regulation module configured to acquire the patient's weight, determine a voltage value corresponding to the patient's weight according to a pre-stored relationship between the patient's weight and the voltage value, and send the voltage regulation signal to the phase shifter to regulate the operation voltage of the phase shifter to the determined voltage value.

9. The MR RF subsystem of claim 8, wherein the voltage regulation module is provided in a computer control subsystem of an MR imaging system.

10. A coil decoupling method for a magnetic resonance (MR) radio frequency (RF) subsystem comprising:
 a body coil and a surface coil both configured to receive MR signals and configured to decouple from each other;
 a preamplifier configured to amplify the MR signals received by the body coil; and
 a phase shifter electrically connected between the preamplifier and the body coil; the coil decoupling method comprises:
 determining a voltage value according to a pre-stored relationship between a patient's weight and the voltage value, wherein the voltage value corresponds to a phase of the phase shifter that is configured to compensate for a decrease in signal decoupling between the body coil and the surface coil caused by the patient's weight;
 sending a voltage regulation signal to the phase shifter to regulate an operation voltage of the phase shifter to the determined voltage value; and
 shifting, by the phase shifter, phase of the MR signals received by the body coil according to the voltage regulation signal.

11. The coil decoupling method of claim 10, wherein, in the pre-stored relationship, the voltage value increases as the patient's weight increases.

12. The coil decoupling method of claim 10, further comprising:
 acquiring the patient's weight and measuring an output impedance of a transmission line between the body coil and the preamplifier, during a scan on the patient;
 regulating a phase of the transmission line by regulating the operation voltage of the phase shifter, until the measured output impedance is equal to an optimized value; and
 storing the relationship between an operation voltage and the patient's weight.

13. The coil decoupling method of claim 12, wherein measuring the output impedance of the transmission line between the body coil and the preamplifier comprises connecting a simulation equipment at a contact point of the transmission line and the body coil to acquire the output impedance of the transmission line.

* * * * *